United States Patent [19]

Murakami et al.

[11] 4,026,927
[45] May 31, 1977

[54] NOVEL PROSTAGLANDIN DERIVATIVES

[75] Inventors: Masuo Murakami; Noriyoshi Inukai, both of Tokyo; Hidenori Iwamoto, Ageo; Toshinari Tamura; Isao Yanagisawa, both of Tokyo; Osamu Hasegawa, Fukuoka; Yoshio Ishii, Omiya; Hideya Matsuda, Urawa; Tetsuya Shiozaki, Misato; Kenichi Tomioka, Kitamoto, all of Japan

[73] Assignee: Yamanouchi Pharmaceutical Co., Ltd., Tokyo, Japan

[22] Filed: Sept. 23, 1974

[21] Appl. No.: 508,252

[30] Foreign Application Priority Data

Sept. 25, 1973 Japan .................. 48-107772
Apr. 15, 1974 Japan .................. 49-41885

[52] U.S. Cl. .................. 260/514 D; 260/240 R; 260/468 D; 424/317
[51] Int. Cl.² .................. C07C 177/00
[58] Field of Search .................. 260/468 D, 514 D

[56] References Cited

UNITED STATES PATENTS 3,816,393   6/1974   Hayashi .................. 260/209

FOREIGN PATENTS OR APPLICATIONS 779,898   8/1972   Belgium .................. 26/468
804,898   3/1974   Belgium .................. 260/468
4,035,275   9/1974   Japan .................. 260/468

Primary Examiner—Robert Gerstl
Attorney, Agent, or Firm—Burgess Ryan and Wayne

[57] ABSTRACT

Novel prostaglandin derivatives are provided having the formula:

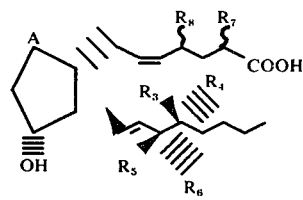

wherein A represents

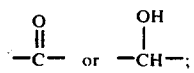

one of $R_3$ and $R_4$ represents a hydrogen atom and the other of them represents a lower alkyl group; one of $R_5$ and $R_6$ represents a hydrogen atom and the other of them represents a hydroxyl group; and one of $R_7$ and $R_8$ represents a hydrogen atom and the other of them represents a lower alkyl group.

The compounds of this invention have excellent effects as prostaglandin $E_2$ and prostaglandin $F_{2\alpha}$.

4 Claims, No Drawings

NOVEL PROSTAGLANDIN DERIVATIVES

DESCRIPTION

The present invention relates to novel prostaglandin derivatives and more particularly, the invention relates to novel prostaglandin derivatives represented by the formula

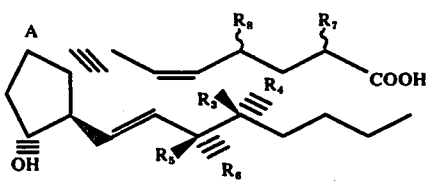

wherein A represents

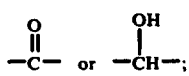

one of $R_3$ and $R_4$ represents a hydrogen atom and the other of them represents a lower alkyl group; one of $R_5$ and $R_6$ represents a hydrogen atom and the other represents a hydroxyl group; and one of $R_7$ and $R_8$ represents a hydrogen atom and the other of them represents a lower alkyl group.

"Lower alkyl group" is meant to include a straight chain or branched chain group having 1–4 carbon atoms.

The prostaglandin derivative of formula 1 can be prepared by hydrolyzing the compound represented by formula II

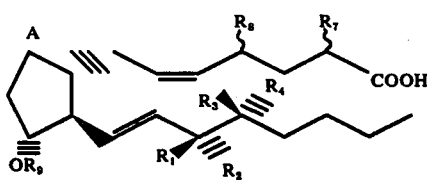

wherein A, $R_3$, $R_4$, $R_7$, and $R_8$ have the same significance as in formula I; one of $R_1$ and $R_2$ represents a hydrogen atom and the other of them represents a hydroxyl group having a protective group; and $R_9$ represents a protective group for hydroxyl group.

Now, examples of the lower alkyl group shown by $R_3$, $R_4$, $R_7$, and $R_8$ of formulae I and II are straight chain or branched chain alkyl groups having 1–4 carbon atoms, such as, for example, a methyl group, an ethyl group, a propyl group, an isopropyl group, a butyl group, etc., and examples of the protective group for the hydroxyl group represented by $R_1$ and $R_2$ of formula II or the protective group represented by $R_9$ of formula II are a group which can be easily released by hydrolysis, such as tetrahydropyran-2-yl group, a trimethylsilyl group, and an acyl group, e.g., an acetyl group, etc.

Also, the dotted line bond to the cyclopentane ring in formulae I and II and additional formulae shown below means that there is an alpha steric configuration, i.e., the substituent is positioned below the plane of the cyclopentane ring and the thick solid line bond means that there is a beta steric configuration i.e., the substituent is positioned above the plane of the cyclopentane ring. Furthermore, the dotted line bond at the side chain means that there is an S steric configuration or an R steric configuration. In addition, in fact, the prostaglandin derivative having the S steric configuration at the dotted line or the R steric configuration or a mixture of such derivatives are obtained as the aimed compound.

Hitherto, prostaglandin $E_2$ ($PGE_2$) shown by the formula

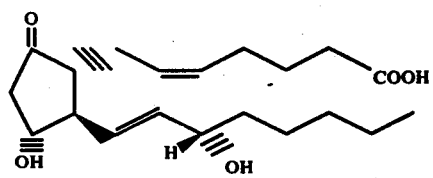

and prostaglandin $F_2\alpha$ ($PGF_2\alpha$) shown by the formula

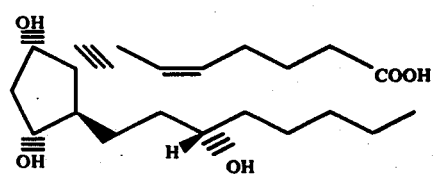

(in the above two formulae the 15-position is in a S steric configuration) are well known as prostadienic acid derivatives having various biological activities and also prostadienic acid derivatives having an alkyl group at the 16-position are reported in the specification of Japanese Patent Application Laid Open No. 53,068/'73.

However, the dialkylprostadienic acid derivatives having lower alkyl groups at the 4- and 16-positions or at 2- and 16-positions as the compounds of this invention are not known. The compounds of this invention have similar biological activities to those of $PGE_2$ and $PGF_{2\alpha}$ but the activities of the compounds of this invention are more superior to those of the known materials. Further, they are more selective in their activities.

The subject compounds of this invention are superior in such biological effects as the contractive effect on smooth muscle (uterus, small intensine, etc.), the hypotensive effect, the hypertensive effect, as well as the antilipolysis effect, the effect of inhibition of gastric juice secretion, the effect on central nervous system, the effect of preventing the reduction in the blood platelet adhesiveness, the blood platelet aggregation, and the formation of thrombus, the effect on proliferation of epidermis, the stimulatory effect on cornification, etc. Therefore, the compounds of this invention are useful for studying, preventing, and reducing various diseases or undesirable physiological states in men and animals. For example, the compounds of this invention are expected to be useful as the agent for preventing atonic uterine hemorrhage after abortion or partus, the odynagoga agent, the agent for interruption of pregnancy, the ovulation control agent, the hypotensive diuretics agent, the agent for curing thrombus, the bronchodilator agent, the anti-ulcer agent, the anti-arteriosclerotic agent, etc.

For producing the compounds of this invention shown by formula I, the 2,16- or 4,16-diloweralkylprostadienic acid derivative of formula II having a protected hydroxyl group may be hydrolyzed under an acid, neutral, or alkaline condition. Typically, when the protective group for the hydroxyl group of the starting material of formula II is a tetrahydropyran-2-yl group, a trimethylsilyl group, etc., the starting material may be hydrolyzed in an organic solvent such as tetrahydrofuran, ethyl acetate, etc., in the presence of an acid such as acetic acid or a neutral condition at room temperature or under heating at, preferably, 40°–50° C. and when the protective group for the hydroxyl group of the starting material of formula II is an acyl group such as an acetyl group, the starting material may be prepared by hydrolyzing in an organic solvent such as methanol, tetrahydrofuran, etc., at room temperature or under heating under an alkaline condition, for example, in the presence of an alkali such as sodium hydroxide, potassium hydroxide, potassium carbonate, etc.

In addition, the compound of formula II wherein A is

may be obtained by reacting the compound of formula II wherein A is

with an oxidizing agent. In this case, examples of the oxidizing agent used are John's reagent, i.e., acidic chromic acid (see, "The Merck Index," 8th Ed., page 1182); a Colin's reagent, i.e., a complex compound of pyridine and chromic anhydride; a bichromate, a permanganate, etc., and among those oxidizing agents, the John's reagent is particularly useful.

In the practice of the production of the prostaglandin derivatives of this invention, a compound of formula II herein, wherein, for example, A is

is dissolved in an organic solvents such as ether and then a John's reagent is added in a slightly excessive amount to the theoretical amount to the solution with stirring, under cooling.

After the reaction is completed, the reaction mixture is washed with cold water and then the ether layer formed is recovered and concentrated under a reduced pressure whereby the oxidation product is obtained as an oily product. In this case, the reaction mixture containing the oxidation product (formula II,

may be subjected to the hydrolysis reaction without isolating the oxidation product.

The compounds of this invention represented by formula I may be separated and purified by an ordinary chemical operation such as extraction, column chromatography, etc.

Examples of the starting materials of formula II used in this invention are illustrated below:

9α-hydroxy- or 9-oxo-2,16-dimethyl-11α,15(S)-bis(-tetrahydropyran-2-yloxy)-5-(cis)-13(trans)-prostadienic acid, 9α-hydroxy- or 9-oxo-2,16-dimethyl-11α,15(R)-bis(-tetrahydropyran-2-yloxy)-5(cis)-13(trans)-prostadienic acid, 9α-hydroxy- or 9-oxo-2,16(S)-dimethyl-11α,15(S)-bis(tetrahydropyran-2-yloxy)-5(cis)-13(trans)-prostadienic acid, 9α-hydroxy- or 9-oxo-2,16(R)-dimethyl-11α,15(S)-bis(tetrahydropyran-2-yloxy)-5(cis)-13(trans)-prostadienic acid, 9α-hydroxy- or 9-oxo-2,16(S)-dimethyl-11α,15(R)-bis(tetrahydropyran-2-yloxy)-5(cis)-13(trans)-prostadienic acid, 9α-hydroxy-2,16(R)-dimethyl-11α,15(R)-bis(tetrahydropyran-2-yloxy)-5(cis)-13(trans)-prostadienic acid, 9α-hydroxy-4,16(R)-dimethyl-11α,15(S)-bis(tetrahydropyran-2-yloxy)-5(cis)-13(trans)-prostadienic acid, 4,16(R)-dimethyl-9-oxo-11α,15(S)-bis(tetrahydropyran-2-yloxy)-5-(cis)-13(trans)-prostadienic acid, etc.

In addition, the starting material of formula II for producing the compound of this invention are novel materials and thus the method of producing the starting materials of formula II will be shown below as reference examples.

Typical compounds of this invention of formula I:

11α,15(S)-dihydroxy-2,16(R)-dimethyl-9-oxo-5(cis)-13-(trans)-prostadienic acid (Compound A), 11α,15(S)-dihydroxy-4(R),16(R)-dimethyl-9-oxo-5(cis)-13-(trans)-prostadienic acid (Compound B), 11α,15(S)-dihydroxy-4(S),16(R)-dimethyl-9-oxo-5(cis)-13-(trans)-prostadienic acid (Compound C), and 9α,11α,15(S)-trihydroxy-4(S),16(R)-dimethyl-5(cis)-13-(trans)-prostadienic acid (Compound D), where compared with two naturally occurring prostaglandins called $E_2$ and $F_{2\alpha}$ with respect to the effect of the inhibition of gastric juice secretion, the hypotensive effect, and the contractive effect on smooth muscle. The experiments and results are as follows:

INHIBITORY EFFECT ON GASTRIC ACID SECRETION

Experiment

By a rat gastrin-perfusion technique (see, M. W. Ghosh and H. O. Schild, "Brit. J. Pharmacol.", 13, 54(1958) and Yutaka Matsuo, "Igaku no Ayumi (Process of Medicine)," 63(5), 235 (1967), the influence of intravenous administered test substances after injection of 3.75 kg. of tetragastrin (made by Nippon Seiyaku K. K.) (hereinafter, it is called TG) on the gastric acid secretion was determined. In addition, male Wistar rats (260–320 g body weight) were used and they were previously fasted for 36 hours. The results are shown in Table I in which the inhibitory effect of gastric acid secretion by prostaglandin $E_2$ is calculated 1.

TABLE I

| Test substance | Inhibition effect on gastric acid secretion |
| --- | --- |
| Prostaglandin E$_2$ | 1 |
| Compound A | 2–5 |
| Compound B | 20 |
| Compound C | 20 |

HYPOTENSIVE EFFECT

Experiment

Femoral arterial blood pressure after intravenous injection of test substances was measured with a pressure transducer, MP-4T type (made by Nihon Kogaku K. K.) in dogs anesthetized with sodium pentobarbital.

The result is shown in Table II in which the hypotensive effect by prostaglandin E$_2$ is calculated 1.

TABLE II

| Test substance | Hypotensive effect |
| --- | --- |
| Prostaglandin E$_2$ | 1 |
| Compound C | 2–3 |

In addition, the comparison results between a known compound, 11α,15α-dihydroxy-16(R)-methyl-9-oxo-5(cis)13(trans)prostadienic acid (hereinafter, called "compound H") and Compounds B and C are shown in the following table.

TABLE II′

| Test substance | Inhibition effect on gastric acid secretion | (a)/(b)* |
| --- | --- | --- |
| Compound B | 20 | 20/1 = 20 |
| Compound C | 20 | 20/3 ≈ 7 |
| Compound H | 20–30 | 20–30/19 ≈ 1–1.6 |

(*)(a)Inhibition effect on gastric acid secretion
(b)Hypotensive effect

As shown in Table II′, Compounds B and C are superior to Compound H in selectivity of inhibition effect on gastric acid secretion.

SMOOTH MUSCLE STIMULATING EFFECT

Experiment

Smooth muscle stimulating effects were evaluated with isolated guinea-pig ileum with Magnus apparatus. The result is shown in Table III in which the smooth muscle stimulating effect by prostaglandin F$_2$ is assumed to be 1.

TABLE III

| Test substance | Smooth muscle stimulating effect |
| --- | --- |
| Prostaglandin E$_2$ | 1 |
| Compound C | 3 |

Also, the result is shown in Table IV in which the smooth muscle stimulating effect by prostaglandin F$_2α$ is assumed to be 1.

TABLE IV

| Test substance | Smooth muscle stimulating effect |
| --- | --- |
| Prostaglandin F$_2α$ | 1 |
| Compound D | 1–3 |

REFERENCE EXAMPLE 1-A

Preparation of 9α-hydroxy-2,16-dimethyl-11α,15(S)-bis(tetrahydropyran-2-yloxy)-5(cis)-13(trans)-prostadienic acid Compound 3a)

After reducing 404 mg. of 4β-(3(S)-tetrahydropyran-2-yloxy-4-methyl-1-trans-octenyl)-1-oxo-5α-tetrahydropyran-2-yloxy-2,3,3aβ,6aβ-tetrahydrocyclopenteno[b]furan in dessicated toluene at temperatures below −60° C., under nitrogen steam using 2 equivalents of diisobutylaluminum hydride, 380 mg. of 2-hydroxy-4β-(3(S)-tetrahydropyran-2-yloxy-4-methyl-1-trans-octenyl)-5α-tetrahydropyran-2-yloxy-2,3,3aβ,6aβ-tetrahydrocyclopenteno[b]-furan (Compound 2a) thus prepared was dissolved in 4 ml. of dessicated dimethyl sulfoxide.

On the other hand, when 960 mg. of the crystal of 2-methyl-5-triphenylphosphonic-pentanic acid bromide was added to the green solution prepared by reacting 193 mg. of 50% sodium hydride dispersed in oil and 5 ml. of dessicated dimethyl sulfoxide under nitrogen stream for about 1 hour at 70° C., a red solution was immediately formed.

To the solution was added dropwise the aforesaid solution of compound 2a under nitrogen stream at temperatures below room temperature and then the reaction mixture was stirred for 2 hours at room temperature.

The reaction mixture was dispersed in a mixture of 100 ml. of ethyl acetate, 50 g. of dry ice, and 20 ml. of water, the organic solvent layer was recovered, and the aqueous layer formed was also recovered and extracted with 50 ml. of ethyl acetate containing 20 g. of dry ice. The extract was combined with the organic solvent layer recovered above and the mixture was washed twice with 20 ml. of ice water, dried over anhydrous magnesium sulfate, and then ethyl acetate was distilled off under a reduced pressure to provide 803.8 mg. of a yellow oily material. When the oily material was purified by means of a column chromatography containing 30 g. of silica gel of 100–200 mesh (made by Kanto Kagaku K. K.) using a mixture of ethyl acetate and n-hexane in volume ratio of 1:1 to 3:1 as an eluate, 193.2 mg. of a colorless transparent oily material (Compound 3a) was obtained.

$[α]_D^{25} = −4.05$ (C = 0.61, chloroform).

REFERENCE EXAMPLE 1-B

Preparation of 9α-hydroxy-2,16-dimethyl-11α,15(R)-bis(tetrahydropyran-2-yloxy)-5(cis)-13(trans)-prostadienic acid (Compound 3b)

To a solution prepared by reacting 5 ml. of dessicated dimethyl sulfoxide and 177.5 of sodium hydride for 1 hour at 70° C. under nitrogen stream was added 880 mg. of 2-methyl-5-triphenylphosphonic-pentanic acid bromide. The red solution obtained was mixed with 347.4 mg. of 2-hydroxy-4β-(3(R)-tetrahydropyran-2-yloxy-4-methyl-1-trans-octenyl)-5α-tetrahydropyran-2-yloxy-2,3,3aβ,6aβ -tetrahydrocyclopenteno[b] fran and by treating the mixture as in Reference Example 1-A, 230 mg. of a colorless transparent oily material (Compound 3b) was obtained.

$[α]_D^{25} = +19.95$ (C = 0.82, chloroform).

REFERENCE EXAMPLE 1-C

Preparation of 9α-hydroxy-2,16(S)-dimethyl-11α,15(S)-bis(tetrahydropyran-2-yloxy)-5(cis)-13(trans)prostadienic acid (Compound 3c)

By following the same procedure as in Reference Example 1-A using 580.7 mg. of Compound 1c, that is, the compound of formula III

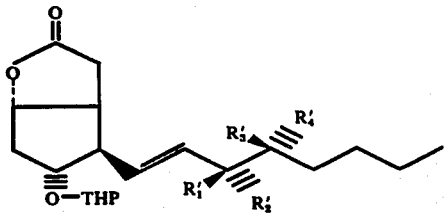

(in which THP is a tetrahydropyran-2-yl group) wherein $R_1'$ is H, $R_2'$ is 0-THP(S), $R_3'$ is $CH_3(S)$, and $R_4'$ is H, 305 mg. of a colorless transparent oily material (Compound 3c) was obtained.

REFERENCE EXAMPLE 1-D

Preparation of 9α-hydroxy-2,16(R)-dimethyl-11α,15(S)-bis(tetrahydropyran-2-yloxy)-5(cis)-13(trans)-prostadienic acid(Compound 3d)

By following the same procedure as in Reference Example 1-A using 392.9 mg. of Compound 1d that is, the compound of formula III wherein $R_1'$ is H, $R_2'$ is 0-THP(S), $R_3'$ is H, and $R_4'$ is CH(R), 263.4 mg. of a colorless transparent oily material (Compound 3d), was obtained.

The nuclear magnetic resonance absorption spectra, the infrared absorption spectra, and the mass spectra of the product suggested the obtention of the subject material.

$[\alpha]_D^{26} = +10.1$ (C = 1.84, chloroform)

REFERENCE EXAMPLE 1-E

Preparation of 9α-hydroxy-2,16(S)-dimethyl-11α,15(R)-bis(tetrahydropyran-2-yloxy)-5(cis)-13(trans)-prostadienic acid (Compound 3e)

By following the same procedure as in Reference Example 1-B using 351.5 mg. of Compound 1e, that is, the compound of formula III wherein $R_1'$ is 0-THP, $R_2'$ is H, $R_3'$ is $CH_3(S)$, and $R_4'$ is H, 306.8 mg. of a colorless transparent oily material (Compound 3e) was obtained.

REFERENCE EXAMPLE 1-F

Preparation of 9α-hydroxy-2,16(R)-dimethyl-11α,15(R)-bis(tetrahydropyran-2-yloxy)-5(cis)-13(trans)-prostadienic acid (Compound 3f)

By following the same procedure as in Reference Example 1-B using 359.2 mg. of Compound 1f, that is, the compound of formula III wherein $R_1'$ is 0-THP(R), $R_2'$ is H, $R_3'$ is H, and $R_4'$ is $CH_3(R)$, 189.6 mg. of the colorless transparent oily material (Compound 3f) was obtained. The nuclear magnetic resonance absorption spectra, the infrared absorption spectra, and mass spectra of the product suggested the obtention of the subject material.

$[\alpha]_D^{26} = +26.6$ (C = 0.92, chloroform).

REFERENCE EXAMPLE 2-A

When a solution of 1.14 g. of 4-carboxy-2-methylbutyltriphenyl phosphonium bromide in 4 ml. of dessicated dimethyl sulfoxide was added at room temperature to the green solution prepared by adding 4 ml. of dessicated dimethyl sulfoxide to 230 mg. of 50% sodium hydride dispersed in oil under nitrogen stream and stirring for 1 hour at 65°–70° C., a red solution was obtained. Then, to the red solution thus obtained was added dropwise under nitrogen stream at room temperature a solution prepared by dissolving 457.2 mg. of 4β-[3(S)-(tetrahydropyran-2-yloxy)-4(R)-methyl-1-trans-octenyl]-2-hydroxy-5α-(tetrahydropyran-2-yloxy)-3aα,4α, 5β, 6, 6aα-hexahydro-2H-cyclopenta[b]furan in 4 ml. of dessicated dimethyl sulfoxide and then the mixture was stirred for 2 hours at 50° C. The reaction mixture obtained was dispersed in a mixture of 100 ml. of ethyl acetate, 40 g. of dry ice, and 50 ml. of water and then the organic solvent layer and the aqueous layer formed were separated each other. The aqueous layer was extracted three times each with 50 ml. of ethyl acetate containing 20 g. of dry ice. The organic solvent layer was combined with the extracts, the mixture was washed twice each with 10 ml. of ice water, dried over anhydrous magnesium sulfate, and then the solvent was distilled off under a reduced pressure to provide 1.8 g. of a yellow oily material. The oily material was purified by a silica gel chromatography using a mixture of ethyl acetate and n-hexane in a volume ratio of 1:1 to 3:1 as an eluant while tracking by a thin-film chromatography, whereby 175.1 mg. of an oily material showing $[\alpha]_D^{21} = +34.2$ (C = 0.8, chloroform)

which indicated the stereoisomer at the 4-position of 9α-hydroxy-4,16(R)-dimethyl-11α,15(S)-bis(tetrahydropyran-2-yloxy)-5(cis)-13 (trans)-prostadienic acid and 111.5 mg. of an oily material showing $[\alpha]_D^{21} = -2.93$ (C = 0.75, chloroform)

was obtained.

EXAMPLE 1

Preparation of 9α,11α,15(S)-trihydroxy-2,16-dimethyl-5 (cis), 13(trans)-prostadienic acid (Compound 4a)

A mixture of 87.5 mg. of compound 3a prepared by the process of Reference Example 1-A and 2 ml. of a 19:11:3 mixture of acetic acid, water, and tetrahydroduran was heated at 40°–45° C. for 2 hours. The reaction mixture was concentrated under a reduced pressure to provide 7.13 mg. of a light-yellow transparent oily material. The oily material was dissolved in ethyl acetate and the solution subjected to a silica gel column chromatography containing 7.5 g. silica gel of 100–200 mesh (made by Kanto Kagaku K. K.). After running 15 ml. of ethyl acetate through the column, the product was eluted with a 100:2:1 mixture of ethyl acetate, methanol, and acetic acid, the fractions containing the desired product were collected and concentrated to provide 32.1 mg. of a colorless transparent oily material (Compound 4a).

$[\alpha]_D^{25} = +37.2$ (C = 0.76, chloroform)

EXAMPLE 2

Preparation of 9α,11α, 15(R)-trihydroxy-2,16-dimethyl-5 (cis), 13(trans)prostadienic acid (Compound 4b)

By following the same procedure as in Example 1 using 86.5 mg. of compound 3b prepared by the procedure of Reference Example 1-B, 40.5 mg. of a colorless transparent oily material (Compound 4b) was obtained.

EXAMPLE 3

Preparation of 9α,11α,15(S)-trihydroxy-2,16(S)-dimethyl-5(cis)-13(trans)-prostadienic acid (Compound 4c)

By following the same procedure as in Example 1 using 117 mg. of compound 3c prepared by the procedure of Reference Example 1-C, 38.4 mg. of a colorless transparent oily material (Compound 4c) was obtained.

$[\alpha]_D^{25} = +34.4$ (C = 0.47, chloroform).

EXAMPLE 4

Preparation of 9α,11α,15(S)-trihydroxy-2,16(R)-dimethyl-5(cis)-13(trans)-prostadienic acid (Compound 4d)

By following the same procedure as in Example 1 using 108.5 mg. of compound 3d prepared by the procedure of Reference Example 1-D, 52.5 mg. of a colorless transparent oily material (Compound 4d) was obtained. The infrared absorption spectra, the nuclear magnetic resonance spectra, and the mass spectra of the product suggested the obtention of the subject compound.

$[\alpha]_D^{25} = +42.0$ (C = 1.8, chloroform).

EXAMPLE 5

Preparation of 9α,11α,15(R)-trihydroxy-2,16(S)-dimethyl-5(cis)-13(trans)-prostadienic acid (Compound 4e)

By following the same procedure as in Example 1 using 158 mg. of compound 3e prepared by the procedure of Reference Example 1-E, 42 mg. of a transparent oily material (Compound 4e) was obtained. The infrared absorption spectra, the nuclear magnetic resonance absorption spectra of the product suggest the desired compound.

$[\alpha]_D^{25} = -12.6$ (C = 0.36, chloroform).

EXAMPLE 6

Preparation of 9α,11α,15(R)-trihydroxy-2,16(R)-dimethyl-5(cis)-13(trans)-prostadienic acid (Compound 4f)

By following the same procedure as in Example 1 using 116.0 mg. of compound 3f prepared by the procedure of Reference Example 1-F, 53.7 mg. of a colorless transparent oily material (Compound 4f) was obtained. The infrared absorption spectra, the nuclear magnetic resonance absorption spectra, and mass spectra of the product suggested the obtention of the subject compound.

$[\alpha]_D^{25} = -1.12$ (C − 1.8, chloroform).

EXAMPLE 7

Preparation of 11α,15(S)-dihydroxy-2,16-dimethyl-9-oxo-5(cis)-13(trans)-prostadienic acid (Compound 5a)

In 4 ml. of ether was dissolved 108.9 mg. of compound 3a prepared by the procedure of Reference Example 1-A and after cooling the solution below 0° C., 3.62 ml. of a cold solution of John's reagent prepared by diluting with water a mixture of 2 g. of chromic anhydride, 9.65 g. of manganese sulfate, and 3.92 g. of concentrated sulfuric acid to 50 ml., was added dropwise to the solution prepared above over a period of 15 minutes, with stirring. The reaction mixture was further stirred for 2 hours at temperatures below 0° C., and then 30 ml. of cold ether and 5 ml. of ice water were added to the reaction mixture followed by shaking well. The resulting ether layer was recovered and the aqueous layer thus formed was saturated with sodium sulfate and then extracted three times each time with 10 ml. of ether. The ether layer was mixed with the ether extracts and the mixture was washed three times each time with 5 ml. of saturated aqueous solution of sodium chloride, dried over anhydrous magnesium sulfate, and then the ether was distilled off under a reduced pressure to provide 104.8 mg. of a light-yellow oily material. To the oily material was added 2 ml. of a 19:11:3 mixture of acetic acid, water, and tetrahydrofuran and after heating the mixture at 40°-45° C. for 1.5 hours, the solvents were distilled off under a reduced pressure to provide 98.7 mg. of a light-yellow oily material.

The oily material was dissolved in ethyl acetate and the solution was subjected to a column chromatography containing 9 g. of silica gel of 100–200 mesh (made by Kanto Kagaku K. K.) and ethyl acetate. After running 10 ml. of ethyl acetate through the column, the aimed product was eluted using a 100:20:1 mixture of ethyl acetate, methanol, and water to provide 37.5 mg. of a colorless transparent oily material (Compound 5a).

$[\alpha]_D^{26} = -72.6$ (C = 0.9, chloroform).

EXAMPLE 8

Preparation of 11α,15(R)-dihydroxy-2,16-dimethyl-9-oxo-5(cis)-13(trans)-prostadienic acid (Compound 5b)

By following the same procedure as in Example 7 using 105.3 mg. of compound 3b prepared by the procedure of Reference Examples 1-B, 25.5 mg of a colorless transparent oily material (Compound 5b) was obtained.

$[\alpha]_D^{26} = -88.2$ (C = 0.85, chlorform).

EXAMPLE 9

Preparation of 11α,15(S)-dihydroxy-2,16(S)-dimethyl-9-oxo-5(cis)-13(trans)-prostadienic acid (Compound 5c)

By following the same procedure as in Example 7 using 158 mg. of compound 3c prepared by the procedure of Reference Example 1-C, 77 mg. of the colorless transparent oily material (Compound 5c) was obtained. The infrared absorption spectra, the nuclear magnetic resonance spectra, and the mass spectra of the product suggested the obtention of the subject compound.

$[\alpha]_D^{25} = -66.0$ (C = 1.2, chloroform).

EXAMPLE 10

Preparation of
11α,15(S)-dihydroxy-2,16(R)-dimethyl-9-oxo-5(cis)-13(trans)-prostadienic acid (Compound 5d)

By following the same procedure as in Example 7 using 152.4 mg. of compound 3d prepared by the procedure of Reference Example 1-D, 90.0 mg. of a colorless transparent oily material (Compound 5d) was obtained. The infrared absorption spectra, the nuclear magnetic resonance absorption spectra, and the mass spectra of the product suggested the obtention of the subject compound.

$[\alpha]_D^{26} = -70.4$ (C = 1.9, chloroform).

EXAMPLE 11

Preparation of
11α,15(R)-dihydroxy-2,16(S)-dimethyl-9-oxo-5(cis)-13(trans)-prostadienic acid (Compound 5e)

By following the same procedure as in Example 7 using 148.5 mg. of compound 3e prepared by the procedure of Reference Example 1E, 44 mg. of a colorless transparent oily material (Compound 5e) was obtained. The infrared absorption spectra, the nuclear magnetic resonance absorption spectra, the mass spectra of the product suggested the obtention of the subject compound.

$[\alpha]_D^{25} = -105.0$ (C = 0.16, chloroform).

EXAMPLE 12

Preparation of
11α,15(R)-dihydroxy-2,16(R)-dimethyl-9-oxo-5(cis)-13(trans)-prostadienic acid (Compound 5f)

By following the same procedure as in Example 7 using 115.3 mg. of compound 3f prepared by the procedure of Reference Example 1-F, 44.3 mg. of a colorless transparent oily material (Compound 5f) was obtained. The infrared absorption spectra, the nuclear magnetic resonance absorption spectra, and the mass spectra of the product suggested the obtention of the subject compound.

$[\alpha]_D^{26} = -107.0$ (C = 1, chloroform)

EXAMPLE 13

To 1.5 ml. of mixture of acetic acid, water, and tetrahydrofuran in volume ratio of 19:11:3 was added 52.1 mg. of an oily material showing $[\alpha]_D^{21} = +34.2$ (C = 0.8, chloroform).

of 9α-hydroxy-4,16(R)-dimethyl-11,15(S)-bis(tetrahydropyran-2-yloxy)-5(cis)-13(trans)-prostadienic acid and the mixture was stirred for 2 hours at 45° C. Then, the solvents were distilled off from the reaction mixture under a reduced pressure and 48.6 mg. of an oily material thus obtained was subjected to a silica gel column chromatography and then using a mixture of ethyl acetate, methanol, and acetic acid in a volume ratio of 100:2:1 as an eluting agent 27.9 mg. of the colorless transparent oily material showing $[\alpha]_D^{21} = +48.8$ (C = 1.1, chloroform).

of 9α,11α,15(S)-trihydroxy-4,16(R)-dimethyl-5(cis)-13(trans)-prostadienic acid was obtained.

EXAMPLE 14

By following the same procedure as in Example 13 using 43.2 mg. of the oily material showing $[\alpha]_D^{21} = -2.93$ (C = C, chloroform).

of 9-hydroxy-4,16(R)-dimethyl-11,15(S)-bis(tetrahydropyran-2yloxy)-5(cis)-13(trans)-prostadienic acid, 22.7 mg. of the colorless transparent oily material showing $[\alpha]_D^{21} = +28.6$ (C = 0.86, chloroform)

of 9α,11α,15(S)-trihydroxy-4,16(R)-dimethyl-5(cis)-13(trans)-prostadienic acid was obtained.

EXAMPLE 15 a. In 3 ml. of ether was dissolved 77.8 mg. of the oily material showing $[\alpha]_D^{21} = +34.2$ (C = 0.8, chloroform).

of 9α-hydroxy-4,15(R)-dimethyl-11,15(S)-bis(tetrahydrofuran-2-yloxy)-5(cis)-13(trans)-prostadienic acid and after cooling the solution to 0° C., 2.5 ml. of a solution prepared by adding water to a mixture of 2 g. of chromic anhydride, 9.65 g. of water-containing manganese sulfate, and 2.13 ml. of concentrated sulfuric acid to a total volume 50 ml. and cooled to temperatures below 0° C. was added to the solution with stirring. The resultant solution mixture was further stirred for 2.5 hours at 0° C. Then, the reaction mixture was dispersed in 30 ml. of cooled ether and the organic solvent layer and the aqueous layer formed were separated. After saturating the aqueous layer with sodium chloride, the aqueous layer was extracted twice each time with 20 ml. of ether. The organic solvent layer recovered above was mixed with the ether extracts, the mixture was washed five times each with 3 ml. of a saturated aqueous solution of sodium chloride, dried over anhydrous sodium sulfate, and then the solvent was distilled off under a reduced pressure to provide 80.8 mg. of the yellow oily material of 4,16(R)-dimethyl-9-oxo-11,15(S)-bis(tetrahydropyran-2-yloxy)-5(cis)-13(trans)-prostadienic acid.

b. To 1.5 ml. of a mixture of acetic acid, water, and tetrahydrofuran in a volume ratio of 19:11:3 was added 80.8 mg. of a yellow oily material of 4,16(R)-dimethyl-9-oxo-11α,15(S)-bis (tetrahydropyran-2-yloxy)-5(cis)-13(trans)prostadienic acid and the mixture was heated at 40°-45° C. for 2 hours. Then, the solvents were distilled off under reduced pressure and 65 mg. of the oily material thus obtained was subjected to a silica gel column chromatography and purified using a mixture of ethyl acetate, methanol, and acetic acid in a volume ratio of 100:2:1 as an eluting agent to provide 30.9 mg. of a colorless transparent oily material showing $[\alpha]_D^{20} = -38.1$ (C = 1.14, chloroform).

of 11α,15(S)-dihydroxy-4,16(R)-dimethyl-9-oxo-5(cis)-13(trans)prostadienic acid was obtained.

EXAMPLE 16

By following the same procedure as in Example (15-a) and (b) using 59.9 mg. of the oily material showing $[\alpha]_D^{21} = -2.93$ (C = 0.75, chloroform).

of 9α-hydroxy-4,16(R)-dimethyl-11α,15(S)-bis(tetrahydropyran-2-yloxy)-5(cis)-13(trans)-prostadienic acid, 24.0 mg. of the colorless transparent oily material showing $[\alpha]_D^{20} = -70.5$ (C = 0.91, chloroform).

of 11α,15(S)-dihydroxy-4,16(R)-dimethyl-9-oxo-5(cis)-13(trans)-prostadienic acid was obtained.

What is claimed:
1. A compound of the formula

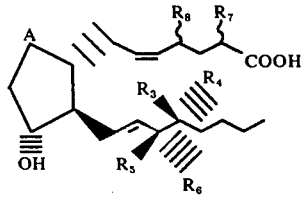

wherein A represents

one of $R_3$ and $R_4$ represents a hydrogen atom and the other of them represents a straight chain or branched chain alkyl group having 1–4 carbon atoms, one of $R_5$ and $R_6$ represents a hydrogen atom and the other of the represents a hydroxyl group, and one of $R_7$ and $R_8$ represents a hydrogen atom and the other of them represents a straight chain or branched chain alkyl group having 1–4 carbon atoms.

2. A compound, according to claim 1, which is 11α,15(R or S)-dihydroxy-2,16-dimethyl-9-oxo-5(cis)-13(trans)-prostadienic acid.

3. A compound, according to claim 1, which is 11α,15(R or S)-dihydroxy-2,16(R or S)-dimethyl-9-oxo-5(cis)-13(trans)-prostadienic acid.

4. A compound, according to claim 1, which is 11α,15(S)-dihydroxy-4,16(R)-dimethyl-9-oxo-5(cis)-13(trans)-prostadienic acid.

* * * * *

UNITED STATES PATENT OFFICE
CERTIFICATE OF CORRECTION

Patent No. 4,026,927      Dated May 31, 1977

Inventor(s) Masuo Murakami, et al

It is certified that error appears in the above-identified patent and that said Letters Patent are hereby corrected as shown below:

Column 4, line 60: "3.75 kg." should read -- 3.75 g. kg. --.

Column 6, line 12: "steam" should read --stream--.

Signed and Sealed this

Tenth Day of January 1978

[SEAL]

Attest:

RUTH C. MASON      LUTRELLE F. PARKER
*Attesting Officer*      *Acting Commissioner of Patents and Trademarks*

UNITED STATES PATENT OFFICE
CERTIFICATE OF CORRECTION

Patent No. 4,026,927      Dated May 31, 1977

Inventor(s) Masuo Murakami et al.

It is certified that error appears in the above-identified patent and that said Letters Patent are hereby corrected as shown below:

Column 4, line 60, "3.75 kg." should read -- 3.75 g./kg. --.

Column 6, line 12, "steam" should read -- stream --.

This certificate supersedes Certificate of Correction issued January 10, 1978.

Signed and Sealed this

Eighteenth Day of April 1978

[SEAL]

Attest:

RUTH C. MASON
Attesting Officer

LUTRELLE F. PARKER
Acting Commissioner of Patents and Trademarks